(12) United States Patent
Huignard et al.

(10) Patent No.: US 8,415,016 B2
(45) Date of Patent: Apr. 9, 2013

(54) HYDROPHOBIC TREATMENT COMPOSITION AND GLAZING

(75) Inventors: Arnaud Huignard, Paris (FR); Khalid Lahlil, Orsay (FR); Sandrine Ithurria, Paris (FR); Thierry Gacoin, Bures sur Yvette (FR); Jean-Pierre Boilot, Meudon la Foret (FR)

(73) Assignee: Saint-Gobain Glass France, Courbevoie (FR)

( * ) Notice: Subject to any disclaimer, the term of this patent is extended or adjusted under 35 U.S.C. 154(b) by 0 days.

(21) Appl. No.: 12/307,927

(22) PCT Filed: Jul. 10, 2007

(86) PCT No.: PCT/FR2007/051625
§ 371 (c)(1),
(2), (4) Date: Mar. 31, 2009

(87) PCT Pub. No.: WO2008/007011
PCT Pub. Date: Jan. 17, 2008

(65) Prior Publication Data
US 2009/0324968 A1    Dec. 31, 2009

(30) Foreign Application Priority Data
Jul. 11, 2006    (FR) ...................................... 06 52914

(51) Int. Cl.
*B32B 9/04*    (2006.01)
(52) U.S. Cl.
USPC ................ 428/429; 428/447; 528/35; 528/42
(58) Field of Classification Search ........................ None
See application file for complete search history.

(56) References Cited

U.S. PATENT DOCUMENTS

| | | | |
|---|---|---|---|
| 2,915,544 A | 12/1959 | Holbrook et al. | |
| 3,146,251 A | 8/1964 | Brown et al. | |
| 3,555,061 A * | 1/1971 | Chapman | 556/459 |
| 4,001,403 A | 1/1977 | Bennett et al. | |
| 5,233,005 A * | 8/1993 | Kobayashi | 528/12 |
| 5,350,824 A * | 9/1994 | Kobayashi | 528/21 |
| 5,997,943 A | 12/1999 | Azzopardi et al. | |

FOREIGN PATENT DOCUMENTS

| | | | |
|---|---|---|---|
| EP | 616 012 A | * | 9/1994 |
| EP | 0 799 873 | | 10/1997 |
| JP | 10-319757 A | * | 12/1998 |
| WO | 2005 084943 | | 9/2005 |

OTHER PUBLICATIONS

Abstract for "Study of the possibility of using cyclodimethylsiloxanes as crown compounds" authored by Yuzhelevskii et al., and published in Vysokomolekulyarne Soedineniya, Seriya B: Kratkie Soobshcheniya (1976) 18 (11), 873-874.*
Machine generated translation of the Specification for JP 10-319757 (1998).*
Machine generated translation of the claims for JP 10-319757 (1998).*

* cited by examiner

*Primary Examiner* — Marc Zimmer
(74) *Attorney, Agent, or Firm* — Oblon, Spivak, McClelland, Maier & Neustadt, L.L.P.

(57) ABSTRACT

Hydrophobic treatment composition comprising one or more compounds, as a mixture, corresponding to the formula

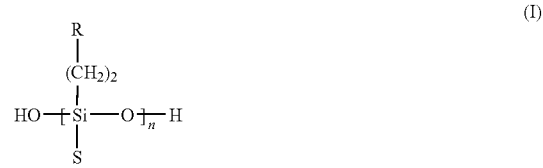

(I)

in which
at least one R is a $C_aF_{2a+1}$ group, a being an integer,
it being possible for another R to be an $SiX_{3-b}RC^1_b$ group, b being 0, 1 or 2
X being a hydrolysable group, such as alkoxy, hydroxyl or halo
$R^1$ being a hydrocarbon group, such as lower alkyl
S is a hydrogen atom, an OH group, an alkyl group, in particular a lower alkyl group, such as $CH_3$, or an $OSiR^2R^3R^4$ group, $R^2$, $R^3$ and $R^4$ being identical or different and consisting in particular of one of the above-mentioned groups carried by an Si atom, such as $(CH_2)_2$—R, a hydrogen atom, an alkyl group or $OSIR^2R^3R^4$,
n is an integer $\geq 1$,
the total number of Si atoms not exceeding 20.
Process for treatment by this composition.
Hydrophobic glass substrate thus obtained and its application, in particular as glazing.

11 Claims, 3 Drawing Sheets

Figure 1:
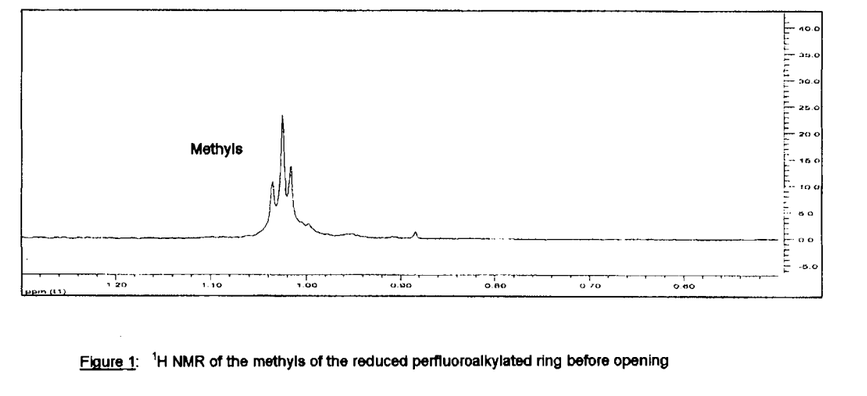

Figure 1: $^1$H NMR of the methyls of the reduced perfluoroalkylated ring before opening Figure 2: $^1$H NMR of the methyls of the reduced perfluoroalkylated ring after opening in potassium hydroxide medium Figure 3: Chromatograms with two equivalents of potassium hydroxide with respect to the ring Figure 4: Change in three entities over time as a function of the number of equivalents of potassium hydroxide introduced

HYDROPHOBIC TREATMENT COMPOSITION AND GLAZING

The present invention relates to the field of hydrophobic substrates, in particular "rain-repellent" glazings, for the construction industry or transport vehicles.

The hydrophobic functionality is achieved by the ease with which drops of water, in particular of rain, flow over the surface of the glazing, either by gravity, over a sufficiently sloping glazing, or under the pressure of the air at the surface of the windshield of a moving automobile, for example.

Patent EP 799 873 describes a glazing hydrophobic treatment composition in which the hydrophobic agent is a fluorinated alkoxysilane of formula:

$$F_3C—(CF_2)_m\text{-}(CH_2)_n Si\,(OR)_{3-p}R'_p$$

in which
m is an integer between 0 and 15,
n is an integer between 1 and 5,
p=0, 1 or 2,
R is an alkyl group,
R' is an alkyl group or a hydrogen atom.

This hydrophobic agent is deposited in a system of aqueous solvent(s) comprising at least one alcohol and water and at least one catalyst chosen from a Bronsted acid and/or base, the proportion of water with respect to the alcohol being between 3 and 20% by volume.

The hydrophobic layer is deposited on a silica sol/gel primer.

However, in view of the numerous mechanical stresses (abrasion, wiping) and weather-related stresses (corrosion by salt, UV radiation, acid rain, and the like), this coating has a durability, of approximately 3 years for automobile side windows and of approximately 1 year for windshields, which can be improved.

A more durable hydrophobic layer was thus prepared according to application WO 2005/084943. The hydrophobic layer is deposited here on a surface with an essentially inorganic composition comprising silicon which occurs in an activated state. The latter can result from said surface having just been prepared by an appropriate process, or from said surface having just been subjected to an appropriate treatment, such as glass dealkalization or attack on silica by a fluorine plasma with creation of an RMS roughness of between 0.1 and 40 nm.

The surface in its activated state can also be electrostatically charged.

The hydrophobic property is contributed by the fluorinated alkoxysilane described above. However, while the durability is markedly improved, the hydrophobic functionality, expressed by the ability of the glazing to discharge drops of water under a stream of air, is reduced.

The inventors thus set themselves the aim of developing a hydrophobic coating which makes possible spontaneous discharge of drops of water at lower vehicle speeds as this functionality is increasingly required by automobile manufacturers in particular. The inventors have, on the other hand, taken care to maintain an acceptable durability of the coating, the reduction in the rate of spontaneous discharge of drops of water contributing thereto by a reduction in wiping and thus in the mechanical stresses. They have thus defined a novel family of hydrophobic agents which makes it possible to achieve their objective.

A subject matter of the invention is thus a hydrophobic treatment composition comprising one or more compounds, as a mixture, corresponding to the formula (I)

in which at least one R is a $C_aF_{2a+1}$ group, a being an integer, it being possible for another R to be an $SiX_{3-b}R_b^1$ group, b being 0, 1 or 2

X being a hydrolysable group, such as alkoxy, hydroxyl or halo $R^1$ being a hydrocarbon group, such as lower alkyl

S is a hydrogen atom, an OH group, an alkyl group, in particular a lower alkyl group, such as $CH_3$, or an $OSiR^2R^3R^4$ group, $R^2$, $R^3$ and $R^4$ being identical or different and consisting in particular of one of the above-mentioned groups carried by an Si atom, such as $(CH_2)_2$—R, a hydrogen atom, an alkyl group or $OSiR^2R^3R^4$, n is an integer $\geq 1$, the total number of Si atoms not exceeding 20.

The number of Si atoms of the compounds preferably does not exceed 10 and particularly preferably 5.

Preferably, the composition of the invention comprises one or more compounds, as a mixture, chosen from -continued $$\begin{array}{cccc}
& SiX_{3-b}R^1{}_b & C_6F_{13} & C_6F_{13} \\
& | & | & | \\
& (CH_2)_2 & (CH_2)_2 & (CH_2)_2 \\
& | & | & | \\
HO-&Si-O-&Si-O-&Si-OH \\
& | & | & | \\
& CH_3 & CH_3 & CH_3
\end{array}$$

$$\begin{array}{cccc}
& C_6F_{13} & SiX_{3-b}R^1{}_b & C_6F_{13} \\
& | & | & | \\
& (CH_2)_2 & (CH_2)_2 & (CH_2)_2 \\
& | & | & | \\
HO-&Si-O-&Si-O-&Si-OH \\
& | & | & | \\
& CH_3 & CH_3 & CH_3
\end{array}$$

$$\begin{array}{cccc}
& SiX_{3-b}R^1{}_b & SiX_{3-b}R^1{}_b & C_6F_{13} \\
& | & | & | \\
& (CH_2)_2 & (CH_2)_2 & (CH_2)_2 \\
& | & | & | \\
HO-&Si-O-&Si-O-&Si-OH \\
& | & | & | \\
& CH_3 & CH_3 & CH_3
\end{array}$$

$$\begin{array}{cccc}
& SiX_{3-b}R^1{}_b & C_6F_{13} & SiX_{3-b}R^1{}_b \\
& | & | & | \\
& (CH_2)_2 & (CH_2)_2 & (CH_2)_2 \\
& | & | & | \\
HO-&Si-O-&Si-O-&Si-OH \\
& | & | & | \\
& CH_3 & CH_3 & CH_3
\end{array}$$

$$\begin{array}{cccc}
& SiX_{3-b}R^1{}_b & C_8F_{17} & C_8F_{17} \\
& | & | & | \\
& (CH_2)_2 & (CH_2)_2 & (CH_2)_2 \\
& | & | & | \\
HO-&Si-O-&Si-O-&Si-OH \\
& | & | & | \\
& CH_3 & CH_3 & CH_3
\end{array}$$

$$\begin{array}{cccc}
& C_8F_{17} & SiX_{3-b}R^1{}_b & C_8F_{17} \\
& | & | & | \\
& (CH_2)_2 & (CH_2)_2 & (CH_2)_2 \\
& | & | & | \\
HO-&Si-O-&Si-O-&Si-OH \\
& | & | & | \\
& CH_3 & CH_3 & CH_3
\end{array}$$

$$\begin{array}{cccc}
& SiX_{3-b}R^1{}_b & SiX_{3-b}R^1{}_b & C_8F_{17} \\
& | & | & | \\
& (CH_2)_2 & (CH_2)_2 & (CH_2)_2 \\
& | & | & | \\
HO-&Si-O-&Si-O-&Si-OH \\
& | & | & | \\
& CH_3 & CH_3 & CH_3
\end{array}$$

$$\begin{array}{cccc}
& SiX_{3-b}R^1{}_b & C_8F_{17} & SiX_{3-b}R^1{}_b \\
& | & | & | \\
& (CH_2)_2 & (CH_2)_2 & (CH_2)_2 \\
& | & | & | \\
HO-&Si-O-&Si-O-&Si-OH \\
& | & | & | \\
& CH_3 & CH_3 & CH_3
\end{array}$$

$$\begin{array}{cccc}
& SiX_{3-b}R^1{}_b & SiX_{3-b}R^1{}_b & SiX_{3-b}R^1{}_b \\
& | & | & | \\
& (CH_2)_2 & (CH_2)_2 & (CH_2)_2 \\
& | & | & | \\
HO-&Si-O-&Si-O-&Si-OH \\
& | & | & | \\
& CH_3 & CH_3 & CH_3
\end{array}$$

$$\begin{array}{ccccc}
& C_6F_{13} & C_6F_{13} & C_6F_{13} & C_6F_{13} \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

$$\begin{array}{ccccc}
& C_8F_{17} & C_8F_{17} & C_8F_{17} & C_8F_{17} \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

$$\begin{array}{ccccc}
& SiX_{3-b}R^1{}_b & C_6F_{13} & C_6F_{13} & C_6F_{13} \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

$$\begin{array}{ccccc}
& C_6F_{13} & SiX_{3-b}R^1{}_b & C_6F_{13} & C_6F_{13} \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

$$\begin{array}{ccccc}
& SiX_{3-b}R^1{}_b & C_8F_{17} & C_8F_{17} & C_8F_{17} \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

$$\begin{array}{ccccc}
& C_8F_{17} & SiX_{3-b}R^1{}_b & C_8F_{17} & C_8F_{17} \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

$$\begin{array}{ccccc}
& SiX_{3-b}R^1{}_b & SiX_{3-b}R^1{}_b & C_6F_{13} & C_6F_{13} \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

$$\begin{array}{ccccc}
& SiX_{3-b}R^1{}_b & C_6F_{13} & SiX_{3-b}R^1{}_b & C_6F_{13} \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

$$\begin{array}{ccccc}
& SiX_{3-b}R^1{}_b & C_6F_{13} & C_6F_{13} & SiX_{3-b}R^1{}_b \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

$$\begin{array}{ccccc}
& C_6F_{13} & SiX_{3-b}R^1{}_b & SiX_{3-b}R^1{}_b & C_6F_{13} \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

$$\begin{array}{ccccc}
& SiX_{3-b}R^1{}_b & SiX_{3-b}R^1{}_b & C_8F_{17} & C_8F_{17} \\
& | & | & | & | \\
& (CH_2)_2 & (CH_2)_2 & (CH_2)_2 & (CH_2)_2 \\
& | & | & | & | \\
HO-&Si-O-&Si-O-&Si-O-&Si-OH \\
& | & | & | & | \\
& CH_3 & CH_3 & CH_3 & CH_3
\end{array}$$

According to other advantageous characteristics of the composition of the invention:
it consists of a basic alcoholic solution;
it comprises from 0.05 to 5% by weight of compound(s) of formula (I).

Another subject matter of the invention is a process targeted at providing or restoring the hydrophobicity of a substrate by the deposition of a composition described above.

According to a first alternative form, this process comprises the preliminary stages consisting in preparing a priming composition obtained from a mixture of a silane $SiX_4$, X being a hydrolysable functional group, with a system of alcohol and aqueous solvent(s) and at least one catalyst chosen from a Bronsted acid and/or base, the content of $SiX_4$ being between 0.001 and 5% by weight of the composition, treating at least the portion of the substrate intended to receive the hydrophobic layer with said priming composition.

According to a second alternative form, this process comprises the preliminary stages consisting in preparing a priming composition obtained from a mixture of a disilane $X_3SiRSiX_3$, X being a hydrolysable functional group and R being a linear, branched or aromatic, preferably linear, alkyl chain in which the number of carbon atoms forming the bond between the two silicon atoms is between 1 and 4, with a system of alcohol and aqueous solvent(s) and at least one catalyst chosen from a Bronsted acid and/or base, the content of $X_3SiRSiX_3$ being between 0.001 and 5% by weight of the composition;

treating at least the portion of the substrate intended to receive the hydrophobic layer with said priming composition.

In accordance with a third alternative form of the process of the invention, the composition defined above is deposited on an essentially inorganic sublayer comprising a silicon content, the surface of which occurs in an activated state.

The activated state has been defined in the introductory part of the application, with reference to application WO 2005/084943.

It is specified that the first and second alternative forms of the process, on the one hand, and the third alternative form, on the other hand, are not mutually exclusive but can be carried out jointly.

Other subject matters of the invention are:

a hydrophobic glass substrate exhibiting an external layer formed from a composition of the invention;

the application of such a glass substrate as glazing for ground, sea or air transport vehicle, glazing for buildings, for street furniture, such as bus shelter, billboard, lamp, for domestic electrical appliances, in particular shelves or doors of refrigerator, freezer, oven, glass-ceramic plate, for interior fittings, such as furniture, shelves, shower stall, aquarium, lighting device, television screen, computer or the like, as ophthalmic glass, for packaging, such as bottle, flask or jar.

The invention is illustrated by the following examples.

EXAMPLE 1

Synthesis of compounds of formula (I).

a) The first stage of the synthesis consists of a perfluoroalkylation, in an anhydrous and solvent-free medium, of 2,4,6,8-tetramethyl-2,4,6,8-tetravinylcyclotetrasiloxane. 1.5 ml of the tetravinylsilicone molecule, i.e. 4.4 mmol, are introduced into a round-bottomed flask and then, in three instalments separated by 2 hours, 7.55 ml of iodoperfluorohexane $CF_3(CF_2)_5I$ (RfI) (i.e. 8 eq., 35 mmol) are added, along with approximately 50 mg of AIBN at each instalment. The combined mixture is brought to reflux at 100° C. overnight under a nitrogen atmosphere. A crude orange-yellow oil is obtained. During this reaction, the RfI can either dimerize, forming the dimmer $CF_3(CF_2)_{10}CF_3$ as product, or become protonated, with the formation of RfH. These secondary products are subsequently removed by drying the reaction products on a vane pump.

After purification, 7.9 g of product are obtained, i.e. a yield obtained of 84%. The proton NMR clearly confirms the purity of the product obtained.

The radical reduction of the iodine atoms is carried out in the presence of tributyltin hydride in a stoichiometric amount and is catalyzed by AIBN in toluene, followed by purification by passing the product through a silica/KF chromatographic column.

The reduction of the ring has to be carried out under an inert atmosphere as tributyltin hydride is very reactive with regard to ambient moisture.

10 ml of toluene, freshly distilled or passed through an alumina column, and 7.8 g of perfluoroalkylated 2,4,6,8-tetramethyl-2,4,6,8-tetravinylcyclotetrasiloxane are introduced into a round-bottomed flask; 70 mg of AIBN are also added. After having left stirring at ambient temperature and under nitrogen for 30 min, 3.95 ml of tributyltin hydride (i.e., one equivalent per iodine) are added through a sleeve-type septum stopper. The round-bottomed flask is subsequently heated at a temperature of 70° C. with stirring overnight.

The mixture obtained is a two-phase medium. The NMR spectra of each of these two phases make it possible to deduce that only the denser phase includes the desired product, while the less dense comprises essentially tin derivatives resulting from the reaction with toluene.

Thus, in a first step, these two phases will be separated by settling.

The product is purified by passing the mixture through a chromatographic column 90% by weight composed of silica (45 g) and 10% by weight composed of potassium fluoride (KF) (5 g). The column is first conditioned with two times 200 ml of ether and then the product, dissolved in ether, is in its turn passed through the chromatographic column.

$Bu_3SnI$ will react on the column with KF to give $Bu_3SnF$, which rapidly reacts with the silica. The purified product in ether is recovered and then dried on a vane pump.

$Bu_3SnI + KF_{aq} \rightarrow Bu_3SnF \downarrow + KI_{aq}$

After purification, 4.9 g of reduced perfluorinated ring are obtained; the yield of the reduction is 82%. The overall yield of the perfluorination is 69%.

The crude product obtained is a very slightly yellow oil which very rapidly crystallizes at ambient temperature.

This product is furthermore insoluble in the majority of conventional organic solvents. Thus, the $^1H$ NMR spectrum can be recorded in deuterated THF, which is a very good solvent for our product, in order to monitor the reaction.

b) As Si—O—Si bonds cleave in basic medium, the ring obtained above is opened in the presence of potassium hydroxide in an alcoholic medium, in order to obtain the linear fluorinated silicone compounds. This is because, although the ring is insoluble in ethanol, once opened it dissolves in this solvent. The reaction is carried out by adding the minimum amount of water necessary for the dissolution of the potassium hydroxide while heating at 40° C.

-continued

The optimization of the amount of potassium hydroxide to be introduced into the reaction medium is studied.

Figure 2:
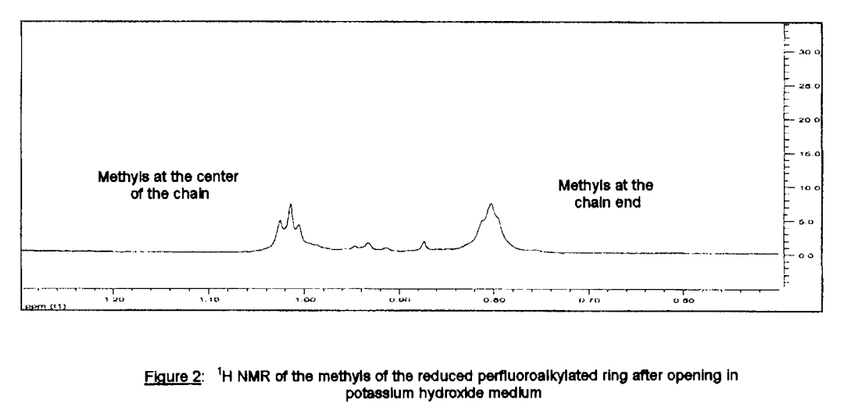

The appended FIGS. 1 and 2 represent the proton NMR analysis of the methyl groups of the perfluoroalkylated 2,4, 6,8-tetramethyl-2,4,6,8-tetravinylcyclotetrasiloxane, known as "reduced perfluoroalkylated ring", before and respectively after the opening in potassium hydroxide medium.

FIG. 2 presents two types of signals, at 1.02 ppm and 0.80 ppm, which can respectively be assigned to the methyls in the middle of —O—Si—O— chains and at the end of —O—Si—OH chains.

The silicon-29 NMR clearly confirms the opening of the ring.

A steric exclusion chromatography study will allow us to optimize the amount of potassium hydroxide to be introduced into the medium in order to obtain fragments of different sizes.

Steric exclusion chromatography is ordinarily used for the study of polymers. We will assume here that we are studying small silicone polymers.

Contrary to conventional methods of chromatography, the physical phenomenon involved in steric exclusion chromatography, which makes possible the separation of different macromolecules, is not based on the chemical affinity with the support but simply on the size of the molecules or more precisely their hydrodynamic volume. This is because the molecules eluted may or may not penetrate into the columns composed of porous beads and thus the smallest molecules are retained whereas the largest molecules elute more rapidly. At the end of the column, detectors can integrate the number of macromolecules exiting from the column at a given instant.

The column used is a G2000HXL column and the detector is a refractometer which calculates a difference in index between that which passes into the column (THF+reaction medium) and the eluent (THF). The solvent used is THF at a flow rate of 0.8 ml/min and the temperature of the column is 25° C.

The basic hydrolysis of perfluorinated 2,4,6,8-tetramethyl-2,4,6,8-tetravinylcyclotetrasiloxane was carried out under the conditions specified above, that is to say in the alcohol with a concentrated potassium hydroxide solution with stirring at 40° C.

The hydrolysis time under consideration is that between the beginning of the hydrolysis and the dilution in THF.

The concentration of the perfluorinated 2,4,6,8-tetramethyl-2,4,6,8-tetravinylcyclotetrasiloxane being set at 3% by weight with respect to the whole of the mixture, the number of equivalents of potassium hydroxide (molar equivalents with respect to the fluorinated ring) was varied:

2 equivalents 5 equivalents 10 equivalents

The chromatograms were recorded for hydrolysis times ranging from 15 minutes to 4 hours. The chromatograms for the opening of the ring with two molar equivalents of potassium hydroxide are presented in FIG. 3. Those following the opening with 5 and 10 equivalents of potassium hydroxide were likewise recorded.

Figure 3:
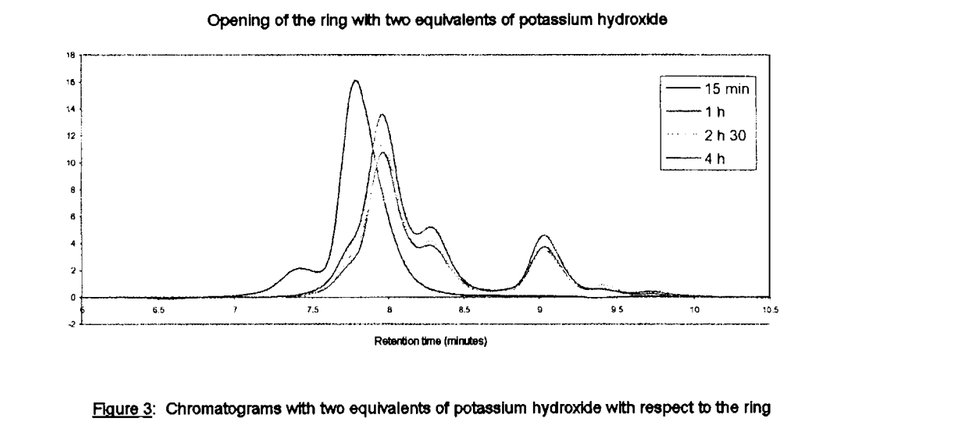

It is noted, from FIG. 3, that, after 15 minutes of hydrolysis, a single peak is visible at 7.8 min which is not detectable at the other hydrolysis times. It corresponds to the closed perfluorinated ring, which finally opens after 1 h of hydrolysis.

Figure 4:
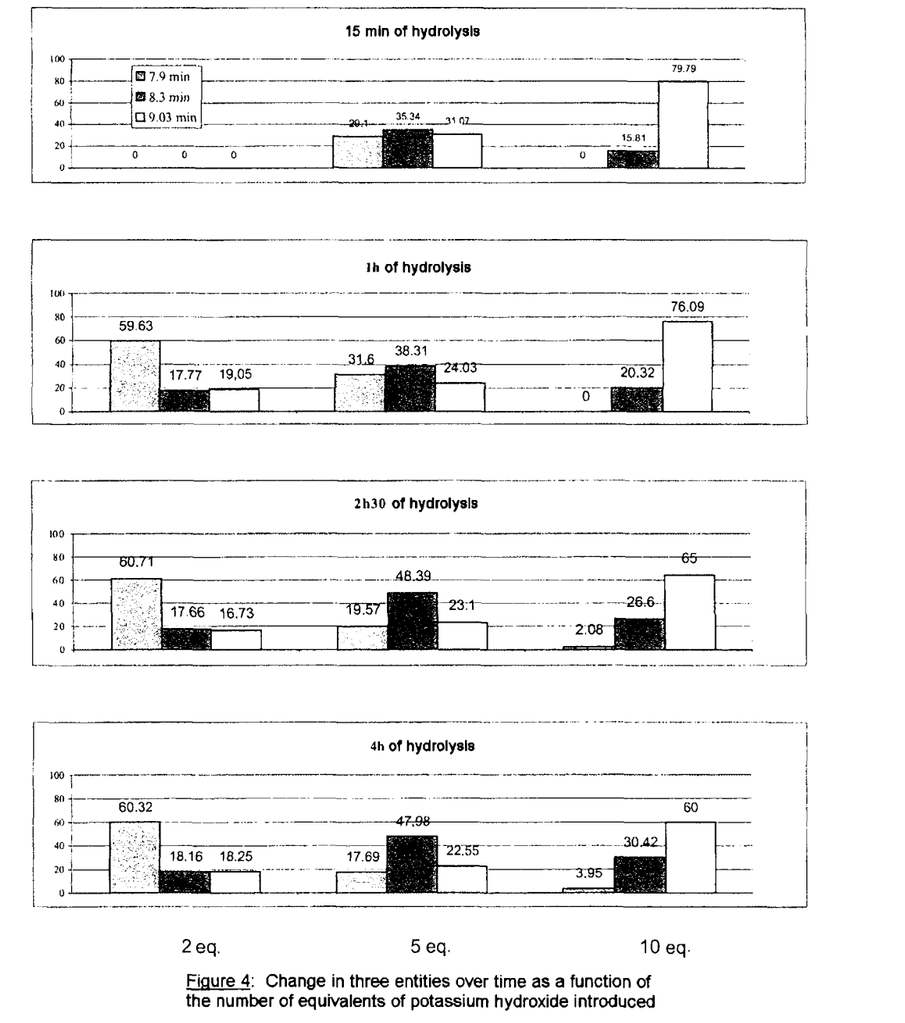

Furthermore, three main peaks are observed at 7.9 min, 8.30 min and 9.0 min, the change in which entities will be plotted over time as a function of the amount of potassium hydroxide added (appended FIG. 4).

From what has been stated, the entities with the shortest retention times are the most condensed. This allows it to be supposed that the entity at 7.9 min corresponds to the fragment comprised in four silicon atoms and the entities at 8.3 min and 9.0 min correspond to linear fragments exhibiting three and two silicon atoms. Entities with longer or shorter retention times are negligible compared with the others.

| Retention time | Assignment |
|---|---|
| 7.8 minutes | Closed ring |
| 7.9 minutes | Fragment comprising 4 silicon atoms |
| 8.3 minutes | Fragment comprising 3 silicon atoms |
| 9.0 minutes | Fragment comprising 2 silicon atoms |

The following conclusions can be drawn from FIG. 4:

with only two equivalents of potassium hydroxide and 15 minutes of hydrolysis, the ring does not open; it is necessary to wait at least one hour for hydrolysis.

with two equivalents of potassium hydroxide, it is the fragment comprising 4 silicon atoms which is predominant, whereas, with 5 equivalents, it is that comprising 3 silicon atoms and whereas, at 10 equivalents, it is that comprising 2 silicon atoms.

with two equivalents of potassium hydroxide, the amounts of each of the fragments remain virtually constant over time, even if condensation is observed to start after 2 h 30 of reaction.

with five equivalents of potassium hydroxide, condensation and fragmentations occur simultaneously. This is because the medium is too basic for the fragment comprising four silicon atoms to remain abundant but the increase in the hydrolysis time induces in parallel a condensation which thus tends to give a predominant linear entity comprising 3 silicon atoms.

Thus, we have shown that the opening of the perfluorinated ring can be carried out simply and rapidly in a potassium hydroxide/ethanol (or isopropanol) medium with a variable amount of potassium hydroxide with respect to the ring. By controlling the amount of alcoholic potassium hydroxide, it proves to be possible to obtain linear fluorinated silicone polymers of predetermined size (2, 3 or 4 silicon atoms).

EXAMPLE 2

Other Synthesis of Compounds of Formula (I)

The double bonds of an octavinyl molecule represented below, referred to as cube, are perfluoroalkylated as in example 1.

The octavinyl molecule is in the solid form (powder) at ambient temperature and at ambient pressure. As it is insoluble in iodoperfluorohexane, it will thus be necessary to find a solvent for this reaction.

After several trials, it was noticed that the octavinyl molecule was soluble under hot conditions only in acetone, toluene, ether and THF and insoluble in alcohols, alkanes and acetonitrile. In point of fact, the perfluoroalkylation reaction is carried out at a fairly high temperature (100° C.) and these solvents (apart from toluene, with a boiling point of 110° C.) have boiling points of the order of 50° C. THF, which exhibits an intermediate boiling point of 70° C., was thus chosen as solvent.

2.5 g of octavinyl molecule, dissolved in 20 ml of THF, are introduced into a round-bottomed flask, followed by the 13.7 ml of RfI (16 eq.) with 100 mg of AIBN, added in three instalments. The reaction mixture is brought to 70° C. under a nitrogen atmosphere overnight.

Perfluoroalkylation of the octavinyl molecule

After reacting overnight, the formation of two phases is observed in the round-bottomed flask, one, a liquid, comprising the THF (which can be easily removed on a vane pump) and the other, which is much more viscous, insoluble in THF. Thus, during the formation of this entity, phase separation of the reaction medium and of the phase formed occurred. Furthermore, the viscous phase is not very soluble under hot conditions.

The two phases were separated using a separating funnel, the viscous phase being dissolved with fluorinated THF and the liquid phase with ethanol.

After drying each of these two phases on a vane pump, 11.43 g of viscous phase and 5.89 g of liquid phase are obtained.

Having obtained two phases corresponding to two different products, they were reduced separately. These reductions were carried out in the same way as for the perfluoroalkylated ring (example 1), that is to say in toluene at 70° C. overnight and under a nitrogen atmosphere.

11.4 g of product from the viscous phase were introduced into a round-bottomed flask, followed by 20 ml of toluene. The reaction mixture was first of all heated with stirring with the exclusion of air, in order for the product to dissolve, at least partially. A catalytic amount of AIBN was subsequently added thereto. The round-bottomed flask is stirred for 30 minutes and finally 5.8 ml of tributyltin hydride (i.e. 8 equivalents) are introduced through a sleeve-type septum stopper.

The reaction mixture is subsequently brought to 70° C. under a nitrogen atmosphere overnight and the product obtained is purified by passing it through a silica: KF column.

4.3 g of purified product are obtained, the yield of the reduction is 50% and that of the overall reaction 34%.

In contrast, the other liquid phase remains inactive with regard to the reduction and does not exhibit any significant proton NMR signal for the Si—CH$_2$-CH$_2$-C$_6$F$_{13}$ groups. We believe that this liquid phase is the addition product of RfI with the solvent (THF), which can open in the presence of radical initiators, such as AIBN. The proton and fluorine NMR spectra clearly confirm this hypothesis.

Reduction of the perfluoroalklated octavinyl molecule

The $^1$H NMR spectrum of the perfluorinated octavinyl molecule was recorded in fluorinated THF using a chloroform capillary including an internal standard: para-xylene. It confirms that the viscous phase obtained at the end of the first stage indeed corresponded to the perfluoroalkylated octavinyl molecule.

The total yield of the perfluorination is 34%.

We used potassium hydroxide with isopropanol as solvent to open the cubic molecule obtained as the boiling point of isopropanol is greater than that of ethanol and we can thus heat the reaction medium to 60° C.

In the same way, once opened, the perfluorinated cube dissolves, even if, at first sight, its solubility appears to be a difficulty.

Furthermore, we attempted to monitor this opening by steric exclusion chromatography but it turned out that the chromatograms obtained were complicated. This is because the cube can fragment into numerous pieces with different conformations although having the same silicon number. From the study carried out on the perfluorinated ring (example 1), it will be assumed that, the more potassium hydroxide in the medium, the more the molecule will fragment.

EXAMPLE 3

Compounds in accordance with the invention are grafted under the same conditions as the first-generation hydrophobic coatings described in the introductory part of the application, with reference to patent EP 799 873.

First of all, the soda-lime-silica float glass surface is brightened with cerium oxide. This is a polishing of the glass with an abrasive powder predominantly comprising microscopic $CeO_2$ particles. It is followed by mechanical rinsing with water finalized by rinsing with demineralized water and then by drying.

Priming is subsequently carried out with a 0.3% by weight solution of tetraethoxysilane (TEOS) in a mixture of 90% by weight of isopropanol and 10% by weight of 0.3M aqueous HCl solution, a mixture subsequently referred to as "hydrolysis mixture". The solution is deposited after a holding time of 15 minutes at ambient temperature from its preparation (hydrolysis time). A layer of $SiO_2$ with a mean thickness of 5 nm is thus formed at the surface of the glass.

Variable concentrations by weight of various hydrophobic agents in the hydrolysis mixture which has just been defined, with hydrolysis times of between 15 minutes and 1 hour, are subsequently deposited.

The contact angle of a drop of demineralized water at equilibrium on a substrate in the horizontal position is measured.

Moreover, the advancing contact angle and the receding contact angle are measured, along with their difference, referred to as hysteresis. The advancing contact and receding contact angles are the limits of the contact angle of a drop on a sloping surface before it becomes detached.

The advancing contact angle is evaluated during the growth (increase of volume) of a drop of water and the receding contact angle during its reduction (decrease in its volume). Growth and reduction are produced using a syringe.

The detachment volumes of a drop of water at inclinations of the glazing of 45 and 90° are also measured. The detachment volume corresponds to the volume starting from which the drop spontaneously detaches from a substrate inclined with respect to the horizontal. This volume is related to the minimum speed of a vehicle for which the drops of rainwater on a windshield are discharged under the effect of a stream of air.

Layers of compounds obtained in the preceding examples are deposited.

These are referred to as ring (according to example 1) or cube (according to example 2).

By way of comparison, the compound $F_{17}C_8$-$(CH_2)_2$—Si$(OEt)_3$, representing the hydrophobic layers of the known art, subsequently referred to as X, is evaluated.

a) Perfluorinated Ring

From the results obtained in steric exclusion chromatography, the perfluorinated ring opens in ethanol for different amounts of potassium hydroxide. Depositions were thus carried out for the following amounts of potassium hydroxide (in an alcohol) and hydrolysis times:

2 equivalents and 1 hour of hydrolysis
5 equivalents and 15 minutes of hydrolysis
10 equivalents and 15 minutes of hydrolysis The results are recorded in the table below. The concentrations of hydrophobic agents are as percentages by weight.

| Characterization of the coatings of the perfluorinated ring | | | |
|---|---|---|---|
| Molecule | $\theta_{water}$ | $\theta_{Advancing}/\theta_{Receding}$ Hysteresis | Detachment volumes (µl) at 45° and 90° |
| 3% Ring 2 eq. of KOH Ethanol | 98.9° ± 1.4° | 108°/84° 24° | 14.5/9.5 |
| 3% Ring 5 eq. of KOH Ethanol | 107.4° ± 0.7° | 118°/98° 20° | 10.2/7.4 |
| 3% Ring 10 eq. of KOH Isopropanol then neutralization | 105.9° ± 0.9° | 113°/95° 18° | 6.3/3.2 |
| 3% X | 108.0° ± 0.9° | 118°/81° 37° | 18.9/10.5 |

It should be pointed out that the solution for the coating comprising ten equivalents of potassium hydroxide was prepared in isopropanol. This is because, in ethanol, the fragments are insufficiently soluble to allow satisfactory grafting to glass.

Furthermore, the solution was neutralized with 0.5 equivalent of HCl with respect to the potassium hydroxide. This is because, in the absence of neutralization, the reaction medium is too basic: the grafting reaction at the surface of the glass is then disadvantageous.

From the table above, it is observed that the substrates exhibit satisfactory contact angles with water and smaller detachment volumes than those obtained with the standard perfluorosilane. The best results are obtained for a number of equivalents of potassium hydroxide equal to 10, which corresponds to a fluorinated dimeric silicone.

b) Perfluorinated Cube

The perfluoroalkylated octavinyl molecule (the cube) was grafted after opening in isopropanol at 60° C. with different amounts of potassium hydroxide for 15 minutes:

2 equivalents
5 equivalents
7 equivalents
10 equivalents

As the strain in the cube is greater than that in the ring, only 15 minutes are needed with two equivalents of potassium hydroxide in order to open it.

The characteristics of the coatings produced with the perfluorinated octavinyl molecule in the presence of a variable amount of potassium hydroxide are combined in the table below:

| Characterization of the coatings of the perfluorinated cube | | | |
|---|---|---|---|
| Molecule | $\theta_{water}$ | $\theta_{Advancing}$/$\theta_{Receding}$ Hysteresis | Detachment volumes (µl) at 45° and 90° |
| 3% Cube 2 eq. of KOH | 109.3° ± 0.3° | 116°/85° 31° | 19.5/12.5 |
| 3% Cube 5 eq. of KOH | 109.3° ± 0.3° | 120°/98° 22° | 17.5/11.5 |
| 3% Cube 7 eq. of KOH | 109.2° ± 0.3° | 119°/99° 20° | 15.5/10.5 |
| 3% Cube 10 eq. of KOH | 103.8° ± 0.3° | 112°/95° 17° | 12.5/7.5 |
| 3% X | 108.0° ± 0.9° | 118°/81° 37° | 18.9/10.5 |

The contact angles with water are satisfactory, with values of the order of 110°.

The detachment volumes vary inversely with the amount of potassium hydroxide introduced into the solution. When the cube is in a medium which is not very basic, the fragments can have highly variable sizes. Thus, once the molecules are grafted, the coating can exhibit a degree of unevenness, resulting in high detachment volumes. However, they remain smaller than those of the known art. The best results are obtained for a number of equivalents of potassium hydroxide equal to 10, which probably corresponds to silicones comprising two or three units

EXAMPLE 4

Hydrophobic layers are deposited on a silica sublayer, the surface of which occurs in an activated state as mentioned in the preamble of the application, with reference to application WO 2005/084943.

This is a silica layer deposited on soda-lime-silica float glass by a plasma enhanced chemical vapor deposition (PECVD) process and on which an RMS roughness of 5 nm had been freshly created, that is to say at most one hour approximately before the deposition of the hydrophobic layer, preferably at most 15 minutes before and particularly preferably at most 5 minutes before.

The RMS roughness is created on the silica sublayer by subjecting it to a plasma treatment by a fluorine-comprising gas, such as $C_2F_6$, in combination with oxygen.

The solution is deposited by wiping on, without brightening or priming, with the same solutions of fluorinated cube or of fluorinated ring as for the depositions on a flat surface (example 3).

Three depositions were carried out, the characteristics of which are combined in the table below:

1: X at 3% in the isopropanol:HCl (90:10) mixture+15 minutes of hydrolysis
2: Perfluorinated ring at 3% with 2 equivalents of potassium hydroxide in isopropanol+1 hour of hydrolysis at 40° C.
3: Perfluorinated cube at 3% with 5 equivalents of potassium hydroxide in isopropanol+15 minutes of hydrolysis at 60° C.

| Characterization of the "silicone" coatings on a rough surface | | |
|---|---|---|
| Molecule and concentration | $\theta_{water}$ | Detachment volumes (µl) at 45° and 90° |
| 3% Ring 2 eq. of KOH Isopropanol | 121.5° ± 2.0° | 26/11 |
| 3% Cube 5 eq. of KOH Isopropanol | 109.7° ± 1.3° | 29/16 |
| 3% X | 109.7° ± 1.3° | 32/18 |

The following observations may be made:

The cubic molecule, due to its size, exhibits a high steric hindrance; this is why it is grafted, once open, less well than the cyclic molecule or the reference X.

The cube and the ring, when they are grafted, level out the roughness. Thus, their detachment volumes are better than that of X which, due to its size, cannot fill in the depressions so well. The first objective is achieved.

Finally, it may be pointed out that the contact angle with water of the ring is excellent.

The spontaneous discharge of the drops of water on a windshield will take place at a lower speed with the silicone coatings according to the invention than with fluorinated silane coatings of the known art. Wiping is thus less frequent, as are the mechanical stresses which result therefrom. This is favorable to an improved durability of the coating.

What is claimed is:

1. A hydrophobic substrate comprising a substrate and a hydrophobic treatment composition deposited on the substrate, wherein the hydrophobic treatment composition comprises (1) one or more compounds corresponding to the formula

(I)

in which
at least one R is a $C_aF_{2a+1}$ group, a being an integer,
optionally, another R is an $SiX_{3-b}R^1{}_b$ group,
b being 0, 1 or 2
X being at least one selected from the group consisting of a hydrolysable alkoxy, hydroxyl and halo group and
$R^1$ being a lower alkyl group
S is at least one selected from the group consisting of a hydrogen atom, an OH group, an alkyl group, and an $OSiR^2R^3R^4$ group, wherein $R^2$, $R^3$ and $R^4$ are identical or different and selected from the group consisting of an $SiX_{3-b}R^1{}_b$ group with b and X as defined above, a hydrogen atom, an alkyl group and an $OSiR^{2'}R^{3'}R^{4'}$ group with $R^{2'}$, $R^{3'}$ and $R^{4'}$ being identical or different and selected from the group consisting of an $SiX_{3-b}R^1{}_b$ group with b and X as defined above, a hydrogen atom and an alkyl group,
n is an integer $\geq 1$, wherein
the total number of Si atoms does not exceed 20 and (2) a basic alcoholic solution.

2. The substrate as claimed in claim 1, wherein the number of Si atoms does not exceed 10.

3. The substrate as claimed in claim 2, wherein the number of Si atoms does not exceed 5.

4. The substrate as claimed in claim 1, wherein the hydrophobic treatment composition comprises one or more compounds chosen from and 5. The substrate as claimed in claim 1, wherein the hydrophobic treatment composition consists of one or more compounds corresponding to the formula (I) and a basic alcoholic solution.

6. The substrate as claimed in claim 1, wherein the hydrophobic treatment composition comprises from 0.05 to 5% by weight of compound(s) of formula (I).

7. A hydrophobic glass substrate comprising the substrate as claimed in claim 1.

8. A glazing for a ground, sea or air transport vehicle, a glazing for buildings, for street furniture, for domestic electrical appliances, for interior fittings for furniture, shelves, a shower stall, an aquarium, a lighting device, a television screen, a computer or the like, ophthalmic glass, and for bottle, flask or jar packaging comprising the glass substrate as claimed in claim 7.

9. A process for providing or restoring hydrophobicity to a substrate comprising depositing a hydrophobic treatment composition on the substrate, wherein the hydrophobic treatment composition comprises (1) one or more compounds corresponding to the formula $$\text{HO}\underset{\underset{S}{|}}{\overset{\overset{R}{|}}{\underset{|}{\overset{|}{\text{Si}}}}}\text{—O}\underset{n}{\underset{\phantom{|}}{\Big]}}\text{H} \qquad (I)$$
$$\underset{\phantom{|}}{(CH_2)_2}$$

in which
at least one R is a $C_aF_{2a+1}$ group, a being an integer,
optionally, another R is an $SiX_{3-b}R^1{}_b$ group,
b being 0, 1 or 2
X being at least one selected from the group consisting of a hydrolysable alkoxy, hydroxyl and halo group and
$R^1$ being a lower alkyl group
S is at least one selected from the group consisting of a hydrogen atom, an OH group, an alkyl group, and an $OSiR^2R^3R^4$ group, wherein $R^2$, $R^3$ and $R^4$ are identical or different and selected from the group consisting of an $SiX_{3-b}R^1{}_b$ group with b and X as defined above, a hydrogen atom, an alkyl group and an $OSiR^{2'}R^{3'}R^{4'}$ group with $R^{2'}$, $R^{3'}$ and $R^{4'}$ being identical or different and selected from the group consisting of an $SiX_{3-b}R^1{}_b$ group with b and X as defined above, a hydrogen atom and an alkyl group,
n is an integer$\geq 1$, wherein
the total number of Si atoms does not exceed 20 and (2) a basic alcoholic solution.

10. The process as claimed in claim 9 wherein the composition is deposited on an essentially inorganic sublayer comprising a silicon content, the surface of which occurs in an activated state.

11. The substrate as claimed in claim 1, wherein the basic alcohol solution comprises water.

* * * * *